United States Patent [19]

Michel

[11] 4,381,293

[45] Apr. 26, 1983

[54] SHAVING COMPOSITION

[76] Inventor: George H. Michel, 343 Oak Knoll Dr., Glendora, Calif. 91740

[21] Appl. No.: 338,349

[22] Filed: Jan. 11, 1982

[51] Int. Cl.³ .......................... A61K 9/00; A61K 7/15; B26B 21/40

[52] U.S. Cl. ......................................... 424/14; 424/73; 424/DIG. 5; 424/16; 30/90

[58] Field of Search ...................... 424/73, DIG. 5, 14, 424/16; 30/90

[56] References Cited

U.S. PATENT DOCUMENTS

| | | | |
|---|---|---|---|
| 2,838,442 | 6/1958 | McMaster | 424/73 |
| 2,857,315 | 10/1958 | Teller | 424/DIG. 5 |
| 3,235,457 | 2/1966 | Laden | 424/73 |
| 3,811,349 | 5/1974 | Jennings | 424/73 |
| 3,956,951 | 5/1976 | Jennings, Sr. | 424/73 |
| 4,011,311 | 3/1977 | Noomen et al. | 424/DIG. 5 |
| 4,291,463 | 9/1981 | Williams | 428/192 |

OTHER PUBLICATIONS

Balsam et al., Cosmetics: Science and Technology, 2nd Ed. vol. 2, pp. 17 and 18 (1972).

*Primary Examiner*—Donald B. Moyer
*Attorney, Agent, or Firm*—Boniard I. Brown

[57] ABSTRACT

This shaving composition comprises a water soluble polyethylene oxide polymer having a molecular weight of 400,000 or less, a tracking agent component, a preservative component, and an anti-caking component. This composition is solid in form and may be molded into a variety of shapes, some of which may be operably attached to a razor.

10 Claims, 2 Drawing Figures

SHAVING COMPOSITION

BACKGROUND OF THE INVENTION

1. Field of the Invention

This invention relates to shaving compositions useful in application during the shaving process. More particularly, this invention relates to shaving compositions comprising water soluble polyethylene oxide polymers. Still more particularly, this invention relates to shaving compositions comprising water soluble polyethylene oxide polymers having a molecular weight less than about 400,000, a tracking agent component, a preservative component, an anti-caking component, a lubricant component, and, optionally, a humectant component.

2. Description of the Prior Art

The American marketplace is replete with a wide variety of shaving compositions. The vast majority of these shaving compositions are soap or surfactant based aerosol foams. These products are heavily advertized and widely used in this country. The more traditionally inclined shaver often employs the shaving brush/soap dish method for applying a preparation to the skin surface prior to the shaving process. However, whatever the process, the shaver must store and handle the relatively bulky containers necessary for these shaving compositions. It would be desirable for a variety of applications if the bulk and weight of the shaving composition could be reduced.

To this end, workers in the field have developed a variety of new shaving compositions. Several of these compositions contain high molecular weight, water soluble polymers and other ingredients to facilitate the passage of the razor blade over the skin surface and to protect the skin from the abrading action of the razor edge. U.S. Pat. No. 3,811,349 and U.S. Pat. No. 3,956,951 both to Joseph Jennings, disclose shaving compositions comprising high molecular weight polyethylene oxide polymers of a molecular weight of about 4,000,000. The earlier reference discloses a solid aqueous solution of the polyethylene oxide polymer while the later reference discloses a simple solvent-free polyethylene oxide tablet. Testing has shown that neither of these compositions is particularly effective.

A somewhat different approach is illustrated in U.S. Pat. No. 4,291,463 to Williams which teaches a polyethylene oxide coating applied to a razor blade for lubrication purposes.

SUMMARY OF THE INVENTION

The formula for this novel shaving composition comprises water soluble polyethylene polymer having a molecular weight of 400,000 or less, a suitable tracking agent component, a preservative component, a lubricant component, and an anti-caking component. Optionally, a humectant component may also be employed. This composition is particularly useful when molded into an effective solid form which can be rubbed over the surface of the user's skin prior to the application of the blade razor. Application of the shaving composition of this invention acts to soften the hair, add moisture to the skin, retain it in place by the action of a micro-protective polymer film layer which, in turn, provides a visual indication to the user (trackability) of the path of the razor blade over the skin surface as well as the extent of the initial coverage of the composition upon application.

DETAILED DESCRIPTION OF THE INVENTION

Figure 1:
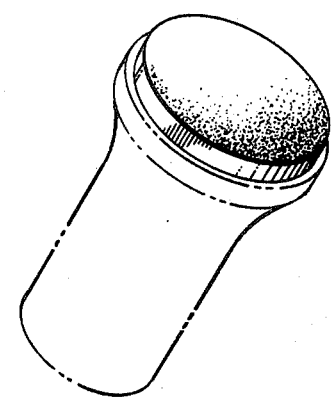
FIG. 1 is an isometric view of a first embodiment of this invention.
Figure 2:
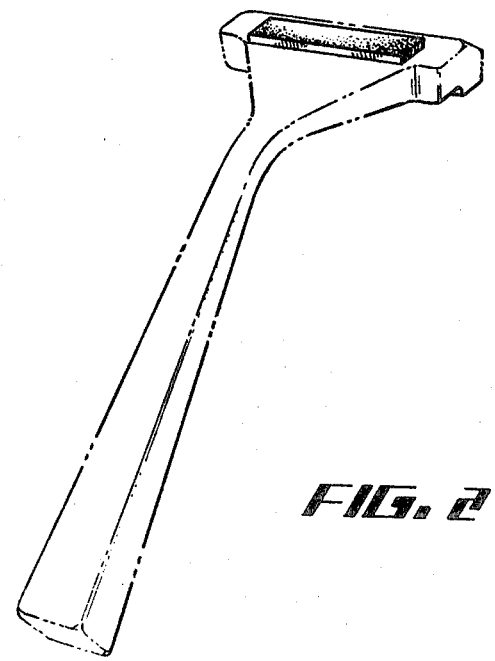
FIG. 2 is an isometric view of a second embodiment of this invention.

A major component in this shaving composition is water soluble polyethylene oxide having a molecular weight of 400,000 or less. The polyethylene oxide polymer is, of course, composed of repeating units of the form:

$$+O-CH_2CH_2+_n$$

wherein the degree of polymerization, n, is such that the molecular weight of the corresponding high polymer is less than about 400,000. This polymer hydrogen bonds strongly with water. One particularly suitable source of supply for this polymer has been Polyox WSR N series of resins produced by the Union Carbide Company. In particular, Polyox WSR N-3000 having an approximate molecular weight of 400,000 has been effective. The polyethylene oxides of molecular weight of 400,000 or less have proven to be particularly effective due to their shear stability characteristics which are necessary for shaving applications, particularly at temperatures in the range of 40° C. to 80° C., especially when compared to polyethylene oxides of higher molecular weight such as those found in the Polyox WSR series which have molecular weights of 600,000 and above. The improved shear stability characteristic allows for consistent uniformity of the polymeric film which is produced when the shaving composition is applied to the skin surface of the user.

The prior art shaving compositions, particularly those which employ polyethylene oxides having molecular weights in the range of 4,000,000, have been shown through testing to be significantly inferior in performance to the shaving composition of this invention which utilizes polyethylene oxides of molecular weights of 400,000 or less. In particular, the high molecular weight polyethylene oxides, when employed as shaving compositions, dry out very rapidly on the skin surface and, consequently, do not allow sufficient time to complete a shaving operation. Additionally, the high molecular weight polyethylene oxide shaving compositions cause the blade razor to clog easily in that these polymers form a gel-like, stringy mixture on the skin surface of the user due to the longer length of these particular molecules. This stringyness problem is not unique to the polyethylene oxides having molecular weights of 4,000,000 and above, since the problem extends down to the range of molecular weights of about 900,000. The use, therefore, of polyethylene oxide polymers of 400,000 molecular weight or less is, therefore, a significant improvement over the water-based polymers disclosed in the prior art.

It has also been found that it is very desirable to provide a trackability characteristic to the shaving composition such that the user can ascertain those portions of the skin surface to which the shaving composition has been applied, and also those portions of the skin surface over which the razor has already passed during the shaving operation. In some instances, it may be desirable to combine a pigment with a fatty acid-based molecule to produce a trackability agent for inclusion into the shaving composition. In general, the longer carbon chain fatty acid molecules will produce compositions with better lubrication and dispersion characteristics, reaching an optimum with lauric acid. The pigments for use in such a trackability agent should be very fine in particle size, in the range of 200 to 400 mesh or finer. A few of the suitable pigments for use in the trackability agent are titanium oxide, zinc oxide, calcium sulphate, calcium carbonate, talc, and diatomaceous earth. In addition to the use of pigments in the trackability agent, it is also possible to incorporate dyes which complex directly with the water soluble polymer. Such dyes, however, should bond semi-permanently to the polyethylene oxide such that the dye is not released to the surface of the skin or elsewhere in order that the overall cleanliness of the shaving operation be maximized. One tracking agent that has displayed excellent characteristics is Igepon, produced and marketed by GAF Corporation. Igepon is a sulfa ethyl ester derived from isothionic acid and a coconut oil-based fatty acid of the general formula $RCOOCH_2CH_2SO_3Na$, where R is an alkyl group. The use of Igepon provides for a shaving composition with excellent tracking characteristics and, further, does not require the addition of a pigment to the composition. Substitutes for Igepon include stearic acid and other soap-forming fatty acids and their alkali metal salts. Detergents suitable for topical application such as Nacconal may also be used as a part of the trackability component.

Additionally, since the prior art compositions do not contain trackability components, such compositions are essentially invisible upon application. When trackability agents are incorporated into these compositions, the stringy texture of the applied composition becomes visually apparent to the user. This visual characteristic has been found to have a decidedly negative effect during consumer testing.

It is common in the formulation of such polymeric compositions to provide for a preservative component within the system such that bacterial and fungal growth are prevented within the composition. Many ingredients are known in the art for this use, including potassium sorbate, glutaraldehyde, methylparaben, propylparaben, sodium edetate, and various combinations thereof. One such combination which has proved to be highly satisfactory for use in the shaving composition of this invention is the combination of methylparaben (p-hydroxy benzoic acidmethyl ester), propylparaben (p-hydroxy benzoic acid propyl ester), and an antimicrobic composition produced by Sutton Labs of Chatham, N.J., comprising imidazolidinylurea, labelled Germall 115.

Another component which has been found to be desirable for inclusion within this shaving composition is an anti-caking agent which aids in flow during the forming of the shaving composition into suitably shaped solids and also prevents lumping during the compression step. Many such chemicals are well known in the art. Particularly useful are silica gels, one of the most effective of which is a synthetic composition produced by Davidson Chemical, a Division of Grace Chemicals, Baltimore, Md., called Syloid 244. Other useful anti-caking chemicals include calcium phosphate, magnesium carbonates, calcium silicate, magnesium silicate, and talc.

Additionally, a lubricant component may be included in the composition. In some situations when the composition is formed into its desired final shape by compression within a mold, the addition of a lubricant component such as magnesium stearate or zinc stearate will act to effectively prevent sticking, packing or capping of a tablet or wafer during its formation.

A further component which may be included in the shaving composition is a humectant material. The humectant aids in providing moisturization for the skin during a shaving operation. One such chemical which has proved to be particularly effective is glycerin. Other useful chemicals include propylene glycol and sorbitol.

The various components may be combined into the shaving composition of this invention in the proportions set forth in Table 1 below.

TABLE 1

| COMPONENT | USABLE RANGE (WT %) |
| --- | --- |
| Igepon | 20%–80% |
| Polyox WSR N-3000 (Polyethelene Oxide) | 1%–65% |
| Methylparaben | 0.05%–2.5% |
| Propylparaben | 0.05%–2.5% |
| Germall 115 | 0.05%–2.5% |
| Syloid 244 | 1%–20% |
| Magnesium Stearate | 0%–10% |

METHOD OF PREPARATION

One formulation of the shaving composition of this invention comprises the following components in the following weight percentages.

| PART A | |
| --- | --- |
| COMPONENT | (WT %) |
| Igepon AC-78 | 66.45 |
| Polyox WSR N-3000 (Polyethelene Oxide) | 28.16 |
| Methylparaben | 0.30 |
| Propylparaben | 0.10 |
| Germall 115 | 0.20 |

| PART B | |
| --- | --- |
| COMPONENT | (WT %) |
| Syloid 244 | 4.79 |
| | 100.00 TOTAL |

The method of preparation for this particular formulation is as follows:

1. Weigh out Part A in a Hobart mixer and blend thoroughly.

2. Wet granulate Part A by adding 20% by weight isopropyl alcohol (99.5% pure) to the above formula for Part A. (NOTE: The granulation step is critical. The isopropyl alcohol should be added slowly but continuously in order that the granulation does not assume a gummy texture.)

3. The granulated mixture is then dried either by spreading it out in trays at room temperature or by oven drying at about 100° for about 24 hours. In either case, the mixture, if prepared correctly, will be sufficiently dry after about 24 hours. Suitable preparation and drying will be evidenced by the relative ease in the handling of the mixture in the following steps.

4. The dried granulation is then screened by passing the composition through a 20-mesh screen.

5. Part B is then added to the screened formulation of Part A. The two components are blended well such that a free-flowing granular powder is formed.

6. The composition is then compressed into the desired solid form using a suitable press.

The shaving composition of this invention may be readily formed into a variety of solid configurations, each adapted to a particular end use. One such configuration is a round disk shaped form of a diameter ranging from about 1 inch to about 3 inches and being from about 1/16 to about ¼ inch thick. The thickness of the disk would be tailored such that a sufficient amount of shaving composition would be present to provide the anticipated number of shaving applications envisioned by the manufacturer of the device. Another suitable form is a rectangular sliver designed to be of suitable size to be adhered to either the razor head or the razor guard of a particular blade type razor. The exact dimensions of the rectangular sliver would, of course, vary depending upon the exact configuration of the blade type razor for which it was designed to be used. However, suitable sizes would range from about 1 inch to about 1¾ inches long by ¼ inch to about ⅜ inch wide by about 1/16 to about ¼ inch thick. The shaving composition of this invention, however, may be readily formed into a variety of other shapes, and the scope of the invention herein should not be read as being limited to the two specific shapes disclosed hereinabove.

I claim:

1. A solid shaving composition comprising:
   a. a water soluble polyethylene oxide polymer of a molecular weight of 400,000 or less in an amount ranging from about 1 to about 65 weight percent;
   b. a trackability component in an amount ranging from about 20 to about 80 weight percent;
   c. a preservative component in an amount ranging from about 0.005 to about 7.5 weight percent;
   d. an anti-caking component in an amount ranging from about 1 to about 20 weight percent;
   e. a humectant component in an amount ranging from about 0.0 to about 20 weight percent; and,
   f. a lubricant component in an amount ranging from about 0.0 to about 10 weight percent.

2. The composition of claim 1 wherein the trackability component comprises Igepon.

3. The composition of claim 1 wherein the trackability component is selected from the group consisting of stearic acid, other soap-forming fatty acids, alkali metal salts of stearic acid and other soap-forming fatty acids, detergents suitable for topical application, and combinations thereof.

4. The composition of claim 1 wherein the preservative component is selected from the group consisting of methylparaben, propylparaben, imidazolidinylurea, and combinations thereof.

5. The composition of claim 1 wherein the anti-caking component comprises silica gel.

6. The composition of claim 1 wherein the humectant component comprises glycerin.

7. A shaving composition comprising:
   a. a water soluble polyethylene oxide polymer of a molecular weight of 400,000 or less in an amount ranging from about 1 to about 65 weight percent;
   b. a trackability component in an amount ranging from about 20 to about 80 weight percent;
   c. a preservative component in an amount ranging from about 0.005 to about 7.5 weight percent;
   d. an anti-caking component in an amount ranging from about 1 to about 20 weight percent;
   e. a humectant component in an amount ranging from about 0.0 to about 20 weight percent; and,
   f. a lubricant component in an amount ranging from about 0.0 to about 10 weight percent
   wherein, the composition is formed into a solid of suitable size and shape for topical application by a user.

8. The shaving composition of claim 7 wherein the solid comprises a disc having a diameter in a range of from about 1.0 inches to about 3.0 inches and a thickness in a range of from about 1/16 inch to about ¼ inch.

9. The shaving composition of claim 7 wherein the solid comprises a rectangular prism having a length of from about 1.0 to about 1.75 inches, a width of from about 0.25 to about 0.375 inches, and a thickness of from about 0.0625 to about 0.25 inches.

10. The shaving composition of claim 7 wherein the solid is operably attached to the razor guard of a blade razor.

* * * * *